United States Patent [19]
Conant

[11] Patent Number: 5,910,512
[45] Date of Patent: *Jun. 8, 1999

[54] TOPICAL ANALGESIC USING WATER SOLUBLE CAPSAICIN

[75] Inventor: Dale Conant, Greenbay, Wis.

[73] Assignee: Healthline Laboratories, Inc., Green Bay, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 08/691,505

[22] Filed: Aug. 2, 1996

Related U.S. Application Data

[63] Continuation of application No. 08/229,202, Apr. 18, 1994, abandoned.

[51] Int. Cl.$^6$ .............................. A01N 37/18; A01N 25/02
[52] U.S. Cl. ........................ 514/617; 514/622; 514/783; 514/817; 514/818
[58] Field of Search .................................. 514/617, 622, 514/783, 817, 818

[56] References Cited

U.S. PATENT DOCUMENTS

| | | | |
|---|---|---|---|
| 4,140,807 | 2/1979 | Braverman | 426/573 |
| 5,178,879 | 1/1993 | Adekunle et al. | 424/484 |

OTHER PUBLICATIONS

Federal Register, External Analgesic Drug Products for Over–the–Counter Human Use; Tentative Final Monograph, Feb. 8, 1983.
Zostrix®, package insert, Marketed by GenDerm Corporation, Lincolnshire, IL 60069, 1994.
ArthriCare™, packaging side panel, Commerce Drug Co., Inc., Farmingdale, NY 11735, 1994.
Omega®, packaging side panel, Block Drug Co., Inc., Jersey City, NJ , 1994.
Capsolin™, packaging side panel, Warner–Lambert Company, Scarborough, Ontario, M1L 2N3, 1994.
Sportscreme®, package insert, Thompson Medical Company, Inc. West Palm Beach, FL 33402–4408, 1994.
Rel–EEZE, packaging side panel, Life's Finest, Marion, IL 62959, 1994.
Icy Hot®, packing side panel, J.W. Gibson Co., Indianapolis, IN, 1994.
Ben–Gay, packaging side panel, Pfizer Canada, Inc., 1994.
Thera–Gesic®, packaging side panel, Mission Pharmacal Company, San Antonio, TX 78296, 1994.
Myoflex, packaging side panel, Fisons Consumer Health, Rochester, NY, 1994.
Watkins® Liniment, bottle label, Watkins, Inc., Winoda, MN 55987 1994.
Zytron, packaging side panel, Sports Injury Products, Inc., Coram, NY 11727, 1994.
Peter S. Dixon, Biology of the Rhodophyta, University of California of Irvine, pp. 220–223, 1973.
Robert C. Weast, Gums, Handbook of Food Additives, The Chemical Rubber Company, pp. 314–329, 1968.
General Carrageenan Application Technology, Application Bulletin, FMC Corporation, 1988.
V.J. Chapman, Seaweeds and Their Uses, Second Edition, Methuen & Co., Ltd., pp. 145–146, 1970.
GW Prescott, The Algaei A Review, Riverside Studies in Biology, Houghton Mifflin Co., pp. 354–355, 1968.
172, Agar, The Merck Index, 11th Edition, p. 31, 1989.
1767, Capsaicin, The Merck Index, 11th Edition, pp. 266–267, 1989.
1769, Capsicum, The Merck Index, 11th Edition, p. 267, 1989.
4212, Furcellaran, The Merck Index, 11th Edition, p. 673, 1989.
1872, Carrageenan, The Merck Index, 11th Edition, pp. 1868–1869, 1989.
Physician's Desk Reference 47th Edition, 1989.
Clinical Pharmacology and Nursing Management, 3rd Edition, 1989.
Nursing 93 Drug Handbook, 1993.
The Nurses Drug Handbook, Delmar Publishers, 6th Edition, 1991.

*Primary Examiner*—Shean C. Wu
*Attorney, Agent, or Firm*—Andrus, Sceales, Starke & Sawall

[57] ABSTRACT

A water-based topical analgesic and method of application wherein the analgesic contains capsicum, capsicum oleoresin and/or capsaicin. This analgesic is applied to the skin to provide relief for rheumatoid arthritis, osteoarthritis, and the like.

12 Claims, No Drawings

TOPICAL ANALGESIC USING WATER SOLUBLE CAPSAICIN

This application is a continuation of U.S. application Ser. No. 08/229,202 filed Apr. 18, 1994, now abandoned.

FIELD OF THE INVENTION

The present invention relates to the method of delivery of capsicum, capsicum oleoresin and/or capsaicin (hereinafter collectively referred to as capsaicin) into the skin as an over-the counter topical analgesic for pain relief. More specifically, this invention relates to a method of delivery of water soluble capsaicin so that it can be applied to the skin and the capsaicin can be absorbed through the skin providing pain relief associated with rheumatoid arthritis, osteoarthritis, neuralgias and the like.

BACKGROUND OF THE INVENTION

Capsaicin is a vanillyl found in hot peppers and related plants. Capsaicin is a derivative of capsicum oleoresin and capsicum. Capsaicin has been proven clinically effective in controlling pain from rheumatoid arthritis, osteoarthritis, painful diabetic neuropathy and neuralgias such as the pain following shingles (herpes zoster). Capsicum provides relief via localized depletion of substance P, a neuropeptide involved in the transmission of pain impulses from the periphery to the central nervous system.

Capsaicin, capsicum and capsicum oleoresin containing 0.025% to 0.25% capsaicin have been recognized by the FDA as an effective over the counter topical analgesic for the temporary relief of minor aches and pains of muscles and joints associated with arthritis, simple backache, strains, bruises and sprains. However, capsaicin is normally not water-soluble. Capsaicin is soluble in solvents such as alcohol, chloroform, ether or petroleum based products. Therefore, a manufacturer of topical analgesial products containing capsaicin must use a form of oil, grease, chloroform, ether, alcohol or a petroleum type product as their base in order to solubilize the capsaicin and subsequently apply it to the skin.

A problem with using an alcohol, chloroform, or ether based analgesic is these harsh chemicals tend to dry out an individual's skin. In addition, patients may experience a warm stinging or burning sensation at the site of application due to these strong solvents.

A problem with the petroleum based analgesics is that the ointments or creams tend to be extremely greasy to the touch and need to be vigorously rubbed onto the skin in order to be absorbed.

SUMMARY OF THE INVENTION

An objective of this invention is to provide a method for using a water soluble capsicum, capsicum oleoresin and/or capsaicin as a topical analgesic to provide pain relief.

Due to the fact that there are no harsh solvents or petroleum by-products, applying the water soluble capsicum analgesic to the skin results in a softening of the epidermal layer. The water soluble capsicum analgesic is also odor free due to the lack of alcohol or other solvents.

This invention is further enhanced by adding various forms of algae (hydrocolloides extracts) to the water soluble capsaicin analgesic. A not so common red algae used in the present invention is ahnfeltia concinna. The three major hydrocolloid extract groups are carrageenan, furcellaran and agar and all three are extracted from a class of red algae call Rodophyceae. All of these red algae extract groups have been used in the past as industrial gums. However, when used as a base in a topical analgesic, they enhance the delivery of capsaicin into the skin thereby further eliminating the need for oils and alcohols.

The carrageenan are noted for their gelling capabilities. The gelling properties of furcellaran yield firm and elastic products that are of similar strength to agar but more firm than carrageenan based products. Agar is the best known of all algae products and is most frequently used in food preparation and orally ingested pharmaceuticals as an emulsifier and as a base for laxatives.

None of the above have ever been used to apply water soluble capsaicin to the skin as a topical analgesic. Because of their stabilizing and gelling properties, capsaicin may be delivered to the skin in a wide range of viscosities, i.e., from watery thin gels to a consistency equivalent of a solid composition.

DETAILED DESCRIPTION OF THE PREFERRED EMBODIMENT

The water soluble capsaicin used in this invention can be obtained from Kalsec, Inc., 3713 West Main, P.O. Box 511, Kalamazoo, Mich. 49005-0511, under the trade designation oleoresin capsicum, water soluble, decolorized, code #01-050-00-06 or #01-020-00-506. In general, the product can be diluted with water so that its total composition falls within the Food and Drug Administration (FDA) requirements (i.e. 0.025% to 0.25% capsaicin). The preferred capsaicin range for this invention is between 0.0025% to 0.25%.

The function of the hydrocolloids in this invention are to form anything from a viscous ointment to a semi-solid gel insothat the capsicum can be applied topically. Specifically, agar is a polysaccharide derived from seaweed (various red algae) and is used as a solidifying agent. Carrageenan is a galactosan sulfate resembling agar in molecular structure. Furcellaran is an extract of red algae which forms a firm, but elastic gel. Agar works best in the range by weight from 0.2% to 5.5%. Furcellaran works best in a range by weight from 0.1% to 7.2%. Carrageenan works optimally in the range by weight from 0.1% to 9.3%.

Capsaicin is a pungent chemical having the name trans-8-methyl-N-vanillyl-6-nonenamide which may be derived from the fruit of various species of *Capsicum Solanaceae*. Capsaicin is also practically insoluble in water, but freely soluble in alcohol, ether, benzene and chloroform. Therapeutically it has been used as a topical analgesic.

The chemical structure of capsaicin is as follows:

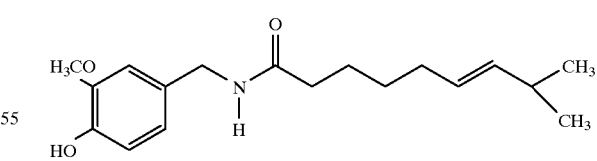

Capsicum oleoresin can be defined as the resins extracted from the dried fruit capsicum. Capsicum oleoresin contains capsaicin as an ingredient therein. Capsaicin is a powerful irritant and prolonged treatment causes insensitivity to painful stimuli. Capsicum is the dried ripe fruit of *Capsicum frutesceens L., Solanaceae* known commercially as African Chillies, and which contains 0.1–1% capsaicin.

In this invention, the function of magnesium oxide is partially as a skin enhancer and also partially to tie up EDTA molecules and the preferred percentage by weight range is from 0.05% to 3.8%.

The function of disodium EDTA is as a preservative by tying up metal ions and is preferred in the range of 0.10% to 20.0%.

EXAMPLE 1

Preparation of topical analgesic containing capsaicin

At room temperature 20.67 pounds of disodium EDTA, 2.37 pounds of magnesium oxide, 64.32 pounds of water, 64.32 pounds of ahnfeltia concinna and 4.75 pounds of water soluble capsicum oleoresin containing 0.025% capsaicin are mixed together. The amount of capsicum oleoresin can be varied up to 10 times more and still fall in the parameters for the FDA as a class one safe and effective topical analgesic.

EXAMPLE 2

Preparation of topical analgesic containing capsaicin

Depending on the strength of the active ingredient desired, mix in propylene glycol at 10 times the amount of capsaicin in a high speed blender. Add this to, at room temperature, 20.67 pounds of disodium EDTA, 2.37 pounds of magnesium oxide, 64.32 pounds of water, 64.32 pounds of ahnfeltia concinna.

EXAMPLE 3

Preparation of topical analgesic containing capsicum

Depending on the strength of the active ingredient desired, to capsicum containing 0.025% capsaicin, add 10 times the amount of propylene glycol, blend thoroughly in blender and add, at room temperature, 20.67 pounds of disodium EDTA, 2.37 pounds of magnesium oxide, 64.32 pounds of water, and 64.32 pounds ahnfeltia concinna.

EXAMPLE 4

Efficacy of Analgesic:

The efficacy of compositions containing capsicum and or capsicum oleoresin in accordance with this invention was determined by the following procedures:

Capsicum, capsicum oleoresin and capsaicin are already proven active ingredients for the following indications according to the FDA CFR 21, page 12, 1983 monograph: For the temporary relief of minor aches and pains of muscles and joints associated with arthritis, simple backache, strains, bruises and sprains. Water soluble capsaicin was suspended in various marine hydrophilic colloid bases with a range of consistencies from watery to solid and applied to the skin of 25 people who have pain. These patients were then asked how these mixtures worked compared to the other products that they were using. The response was that the product worked quickly and was easy to apply. It was noted that all of the forms from watery to solid provided the same fast effective relief and were all easier to apply than traditional products.

Various modes of carrying out the invention are contemplated as being within the scope of the following claims particularly pointing out and distinctly claiming the subject matter regarded as the invention.

Having thus described the invention, what is claimed is:

1. A method of treating localized pain comprising the steps of applying water-based topical analgesic to an individual's epidermal layer wherein the analgesic comprises capsaicin wherein the percentage of capsaicin ranges from 0.0025% to 0.25% by weight, magnesium oxide in a range from 0.005% to 20.0% by weight disodium EDTA in a range from 0.005% to 20.0% by weight and water;

said analgesic prepared by mixing the disodium EDTA in the water to form a mixture, adding the magnesium oxide to the mixture at a ratio of about 1 part magnesium oxide to about 8.7 parts disodium EDTA, and thereafter adding the capsaicin.

2. The method described in claim 1 wherein the topical analgesic contains capsaicin in combination with capsicum oleoresin so that the total percentage of both capsaicin and capsicum oleoresin ranges from 0.0025% to 0.25% by weight.

3. The method described in claim 1 wherein the topical analgesic contains capsaicin in combination with capsicum so that the total percentage of both capsaicin and capsicum ranges from 0.0025% to 0.25% by weight.

4. The method described in claim 1 wherein the topical analgesic contains capsaicin in combination with capsicum oleoresin and capsicum so that the total percentages of capsaicin, capsicum oleoresin and capsicum ranges from 0.0025% to 0.25% by weight.

5. The method described in claim 1 wherein the topical analgesic further contains a hydrocolloid selected from the group consisting of agar, carrageenan and furcellaran, wherein the agar and furcellaran is present in a range from 0.005% to 8.0% by weight and carrageenan is present in a range from 0.005% to 80.0% by weight.

6. The method described in claim 1 wherein the topical analgesic further contains ahnfeltia concinna present in a range from 0.005% to 80% by weight.

7. Topical analgesic comprising capsaicin; wherein the percentage of capsaicin ranges from 0.0025% to 0.25% by weight, magnesium oxide in a range from 0.005% to 20.0% by weight, disodium EDTA in a range from 0.005% to 20.0% by weight, and water;

said analgesic prepared by mixing the disodium EDTA in the water to form a mixture, adding the magnesium oxide to the mixture at a ratio of about 1 part magnesium oxide to about 8.7 parts disodium EDTA, and thereafter adding the capsaicin.

8. The invention described in claim 7 wherein the topical analgesic contains capsaicin in combination with capsicum oleoresin so that the total percentage of both capsaicin and capsicum oleoresin ranges from 0.0025% to 0.25% by weight.

9. The invention described in claim 7 wherein the topical analgesic contains capsaicin in combination with capsicum so that the total percentage of both capsaicin and capsicum ranges from 0.0025% to 0.25% by weight.

10. The invention described in claim 7 wherein the topical analgesic contains capsaicin in combination with capsicum oleoresin and capsicum so that the total percentages of capsaicin, capsicum oleoresin and capsicum ranges from 0.0025% to 0.25% by weight.

11. The analgesic described in claim 7 wherein the topical analgesic further contains a hydrocolloid selected from the group consisting of agar, carrageenan and furcellaran, wherein the agar and furcellaran is present in a range by weight from 0.005% to 5.0% and carrageenan is present in a range by weight of 0.005% to 80.0%.

12. The analgesic described in claim 7 wherein the topical analgesic further contains ahnfeltia concinna present in a range from 0.005% to 80% by weight.

* * * * *